(12) United States Patent
Wayne et al.

(10) Patent No.: US 6,976,494 B2
(45) Date of Patent: Dec. 20, 2005

(54) HAIR COLORANT DISPENSER

(75) Inventors: Jim Wayne, Beverly Hills, CA (US); Debra Dumas, Los Angeles, CA (US)

(73) Assignee: J.W. Industries, Inc., Beverly Hills, CA (US)

( * ) Notice: Subject to any disclaimer, the term of this patent is extended or adjusted under 35 U.S.C. 154(b) by 15 days.

(21) Appl. No.: 10/282,739

(22) Filed: Oct. 29, 2002

(65) Prior Publication Data

US 2004/0079383 A1    Apr. 29, 2004

(51) Int. Cl.$^7$ .......................... A45D 24/16; B67D 5/00
(52) U.S. Cl. ................... 132/108; 222/83; 222/129
(58) Field of Search ........................ 132/208, 221, 132/317–318, 74.5, 108; 401/133, 134; 222/129, 222/81, 83–83.5, 85–86, 145.1; 206/222; 215/DIG. 8

(56) References Cited

U.S. PATENT DOCUMENTS

| | | | | |
|---|---|---|---|---|
| 3,404,811 A | * | 10/1968 | Cernei | 222/83 |
| 4,682,689 A | * | 7/1987 | Pereira et al. | 206/222 |
| 4,757,916 A | * | 7/1988 | Goncalves | 222/83 |
| 4,898,293 A | * | 2/1990 | Morel | 215/250 |
| 5,337,764 A | * | 8/1994 | McKay | 132/116 |
| 5,342,136 A | | 8/1994 | Fukami | |
| 5,692,644 A | * | 12/1997 | Gueret | 222/80 |
| 5,762,077 A | | 6/1998 | Griffiths, Jr. | |
| 5,769,552 A | * | 6/1998 | Kelley et al. | 401/132 |
| 5,778,902 A | | 7/1998 | Nagy | |
| 5,960,802 A | | 10/1999 | Sakai | |
| 6,065,641 A | * | 5/2000 | Laguna Valderrama | 222/80 |
| 6,189,688 B1 | | 2/2001 | Aneas | |
| 6,209,548 B1 | | 4/2001 | Harrison | |

\* cited by examiner

*Primary Examiner*—Kevin Shaver
*Assistant Examiner*—Stephanie L. Willatt
(74) *Attorney, Agent, or Firm*—Marshall A. Lerner, Esq.; Patrick Avakian, Esq.; Kleinberg & Lerner, LLP (57) ABSTRACT

A disposable, solution-mixing hair colorant dispenser: tubular rear segment including first reservoir having rupturable front end; tubular middle segment including second reservoir having rupturable rear and front ends; tubular front segment including rear end and forward-projecting porous applicator. Rupturing member near adjacent ends of first and second reservoirs for rupturing both when first and second segments are engaged. Rupturing member near front end of second reservoir for rupturing same when second and third segments are engaged. Alternative rupturing members: double-ended between first and second reservoirs and single-ended attached to third segment; double-ended within second reservoir; single-ended within first reservoir and single-ended attached to third segment. Segments threaded for endwise engagement to seal segments and rupture reservoirs. Fluids mixed and dispensed through applicator.

5 Claims, 9 Drawing Sheets

HAIR COLORANT DISPENSER

BACKGROUND OF THE INVENTION

1. Field of the Invention

The present invention relates to mixing and dispensing small volumes of liquids (more particularly, hair colorants) and especially to a disposable hand-held container having reservoirs for mixing hair colorant ingredients and an applicator for applying them to a person's hair.

2. Description of the Related Art

Coloring a person's hair may entail preparing an unstable mixture of two or more solutions and applying them to the hair in the short time before they lose their effectiveness. This commonly involves opening several containers, mixing their contents, and perhaps transferring the mixture to yet another container, preferably one having a spout or applicator, from which to pour, drip, or paint the mixture onto the hair. These steps waste time, effort, and material and make a mess.

It would be helpful if the hair stylist could mix the solutions without pouring, apply the mixture without first transferring it, and dispose of the spent containers instead of cleaning and re-using them within the limited space available in most salons.

What is needed is economy of steps, an inexpensive yet highly functional structure, and containment and facile disposal of waste.

SUMMARY OF THE INVENTION

It is an object of the present invention to provide an inexpensive, disposable hair colorant dispenser which preserves separate components of a coloring solution until the time of use, mixes them without opening separate containers and pouring the contents back and fourth, and also functions as a tool for applying the mixture.

It is an additional object of the present invention to provide such a dispenser in which fluid communication is reliably established between a plurality of compartments with simple manipulation of a clean, non-leaking container.

In accordance with these objects and with others which will be described and which will become apparent, an exemplary embodiment of the hair colorant dispenser in accordance with the present invention comprises first, second and third segments;

the first segment comprising a tubular housing having a rear end and having a ruputurable front end adapted for forcible engagement with the second segment, a first reservoir being defined in the first segment; a first rupturing means disposed within the first reservoir to rupture the front end when the first and second segments are forcibly engaged;

the second segment comprising a tubular housing having ends to engage the first and third segments, a second reservoir being defined within the second segment, said second reservoir having rupturable rear and front ends, the rear end also being rupturable by the rupturing means of the first segment when the first and second segments are forcibly engaged;

said third segment comprising a tubular housing, a front end defining an applicator, a rear end for forcible endwise engagement with the front end of the second segment, and second rupturing means attached to the rear end.

Forcible engagement of the first and second segments lets fluid flow between the first and second reservoirs. Forcible engagement of the second and third segments lets fluid flow from the second reservoir to the applicator.

It is an advantage of this embodiment that a single rupturing member reliably pierces two membranes and holds both open.

In another exemplary embodiment of the hair colorant dispenser in accordance with the present invention, at least one of the first and second segments has sealing means for confining a fluid as they are engaged.

In another exemplary embodiment, at least one of the three segments has such sealing means.

In another exemplary embodiment, the front end surface of the first segment can be forced rearwardly onto the rupturing means.

In another exemplary embodiment, the rupturing means has a sharp edge near the front end surface and is supported within the first reservoir so as to resist being pushed rearward when the front end surface is pushed rearward.

In another exemplary embodiment, the applicator includes a porous wick.

In another exemplary embodiment, the front end surface of the third segment is adapted for engagement with the front end surface of the second segment, so that the third segment can be mounted on the front end of the second segment for protection during shipment. It can be removed, reversed and re-attached for use.

In another exemplary embodiment, the rear end surface of the third segment is securely and sealingly engageable with the front end surface of the second segment such that the second rupturing means projects rearward a sufficient distance to rupture the front end surface of the second segment, and the front end surface of the third segment is securely and sealingly engageable with the front end surface of the second segment such that clearance exists for the applicator to be disposed forward of the front end surface of the second segment.

In another exemplary embodiment, each of the first and second rupturing means includes at least one base member fixed relative to the tubular housing and at least one cutting edge disposed distally on the base member. The cutting edge and base member cooperate, when fully engaged with the respective rear and front end surfaces of the second segment, to hold the ruptured surfaces open so that fluids may easily pass between the first, second, and third segments.

In another exemplary embodiment, each of the first and second rupturing means includes several base members joined to form a common cutting edge and to define at least two fluid passages around the base members within the tubular housing.

Another exemplary embodiment of a hair colorant mixing and dispensing apparatus in accordance with the present invetion comprises endwise serially sealingly engageable first, second and third tubular segments, a first rupturing means disposed between the first and second segments, and a second rupturing means disposed between the second and third segments;

the first segment defining an interior including a first reservoir; the second segment defining an interior including a second reservoir; the third segment defining an interior including an applicator communicating with the interior;

the first rupturing means comprising at least one stabilizing member for securing it to an end of at least one of the first and second segments;

the first rupturing means comprising at least one cutting edge fixed to the at least one stabilizing member and disposed toward at least one of the respective ends of the first and second segments, the first rupturing means comprising at least one thrusting member contacting the at least one cutting edge;

the first and second segments when so engaged defining a range of relative longitudinal displacement including first and second relative positions;

engagement in the and second position and all in intermediate positions forming a seal between adjacent ends of the segments to prevent fluid leakage; engagement in the second position resulting in the transmission of force through the at least one thrusting member, thereby rupturing adjacent ends of said segments and holding open the ruptured ends to let fluid pass;

the second rupturing means comprising at least one stabilizing member for securing the second rupturing means to an end of at least one of the second and third segments; the second rupturing means comprising at least one cutting edge fixed to the at least one stabilizing member and disposed toward the end of the second segment;

the second rupturing means comprising at least one thrusting member contacting the at least one cutting edge;

the second and third segments when so engaged defining a range of relative longitudinal displacement including first and second relative positions; engagement in the first, second and all intermediate positions forming a seal between adjacent ends of the segments to prevent fluid leakage;

engagement in the second position resulting in the transmission of force through the at least one thrusting member thereby rupturing an end of the second segment and holding it open.

Engagement of the first, second, and third segments in the second relative positions lets fluid flow between the first and second reservoirs and into the applicator.

It is an advantage of this embodiment that forces are balanced between the cutting edges of the first rupturing member to assure that both membranes between the first and second reservoirs are opened.

In another embodiment of the hair colorant dispenser in accordance with the present invention, the applicator comprises a porous wick.

In another embodiment, the front end surface of the third segment is adapted for engagement with the front end surface of the second segment, whereby the third segment may be mounted on the front end of the second segment so that the applicator is adjacent the front end surface of the second segment for shipment and storage.

In another embodiment, the rear end surface of the third segment is securely and sealingly engageable with the front end surface of the second segment so that the second rupturing means projects rearward a sufficient distance to rupture the front end surface of the second segment; and the front end surface of the third segment is likewise engageable with the front end surface of the second segment so that sufficient clearance exists for the applicator to be disposed forward of the front end surface of the second segment for shipment and storage.

In another embodiment, each of the first and second rupturing means comprises a plurality of base members joined to form a common cutting edge and to define at least two fluid passages around the base members within the housing.

In another embodiment, a first stabilizing member secures a first cutting edge to the first segment and a second stabilizing member secures a second cutting edge to the second segment.

In another embodiment, a first stabilizing member secures a first cutting edge and a second cutting edge to one of the first and second segments.

Another exemplary embodiment of a hair colorant mixing and dispensing apparatus in accordance with the present invetion comprises a first segment, a second segment, and a third segment;

the first segment comprising a tubular body, a closed rear end, and an open front end, the tubular body and the front end being adapted for engagement with the second segment; a first reservoir being defined between the rear end and the front end within the body, the first reservoir comprising a frangible front membrane disposed proximate the front end of the first segment, the first reservoir being stiff enough to resist longitudinal compression;

the second segment comprising a tubular body, an open rear end, and an open front end, the rear end being adapted for endwise engagement with the first segment, the front end being adapted for engagement with the third segment; a second reservoir being defined between the rear end and the front end within the body, the second reservoir comprising a frangible front membrane and a frangible rear membrane;

rupturing means being disposed within the second reservoir and comprising a rear punch disposed proximate the rear end surface of the second reservoir and a front punch disposed proximate the front end surface thereof and longitudinally spaced apart a first length from the rear punch;

the second reservoir being longitudinally compressible such that, when so compressed, the front membrane is disposed less than the first length from the rear membrane;

the third segment comprising a tubular body; a front end defining an applicator, and an open rear end adapted for endwise engagement with the second segment;

the first, second, and third segments cooperating, when engaged, to force the front membrane of the second reservoir rearwardly toward the front punch and to force the front membrane of the first reservoir and the rear membrane of the second reservoir forwardly toward the rear punch;

whereby engagement of the first segment with the second segment lets fluid flow between the first reservoir and the second reservoir, and engagement of the second segment with the third segment lets fluid flow between the second reservoir and the applicator.

It is an advantage of this embodiment that a single rupturing member is utilized to open all three membranes that must be opened to mix and dispense the contents. It is a further advantage that, because the rupturing member is contained within the second reservoir, it is unlikely to be lost or damaged.

Another exemplary embodiment of a hair colorant dispenser in accordance with the present invention further comprises a connector disposed between the front punch and the rear punch for holding the first punch and the second punch in longitudinally spaced-apart relation.

In another exemplary embodiment, the second reservoir defines at least one interior bracing surface and the front punch and the rear punch are supported by the interior bracing surface so as to resist the first punch and the second punch in longitudinally spaced-apart relation.

Also in accordance with the same objects, an exemplary method of mixing and dispensing hair colorant in accordance with the present invention comprises the steps of:

providing front, middle and rear serially endwise engageable tubular dispenser segments;

providing first and second mixture components individually and separately sealed behind a plurality of membranes located in the rear and middle segments;

providing at lest one cutter on at least one of the rear and middle segments, the at least one cutter having at least one force-balancing means assuring that the cutter encounters sufficient resistance penetrating each one of the membranes to be cut by the at least one cutter, that the at least one cutter will substantially open every one of the membranes;

engaging the rear and middle segment to drive the at least one cutter to rupture the membranes and thereby to unseal and mix together the first and second mixture components;

providing an applicator on the front segment; and engaging the middle and front segments to dispense the components through the applicator.

Another exemplary method of mixing and dispensing hair colorant in accordance with the present invention includes the further step of providing a cutter on the front segment.

It is an advantage of the present invention that all membranes that must be ruptured to mix and dispense the contents are reliably ruptured and held open to provide unimpeded fluid flow.

BRIEF DESCRIPTION OF THE DRAWINGS

For a further understanding of the objects and advantages of the present invention, reference should be had to the following detailed description, taken in conjunction with the accompanying drawing, in which like parts are given like reference numbers and wherein:

FIG. 6 is a side view thereof;

DESCRIPTION OF THE PREFERRED EMBODIMENTS

Figure 1:
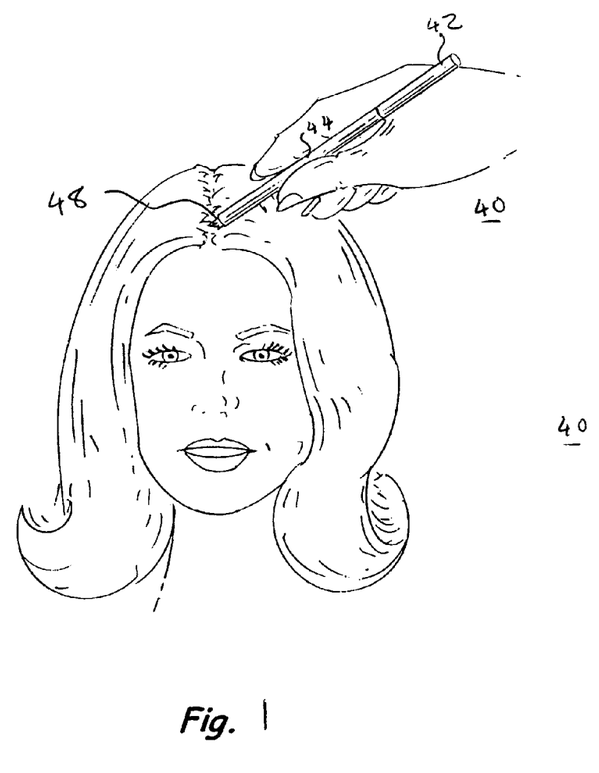
FIG. 1 is a perspective view of an exemplary embodiment of a hair colorant dispenser in accordance with the present invention.

The invention will now be described with reference to FIG. 1, which illustrates in perspective view a preferred embodiment of the hair colorant dispenser 40 ("dispenser") in accordance with the present invention shown generally by the reference number 40 comprising a first segment 42, a second segment 44, and a third segment (not visible in FIG. 1) including a wick-like applicator 48 adapted for dripping, dabbing, or painting the liquid contents of the dispenser 40 onto a person's hair.

Figure 2:
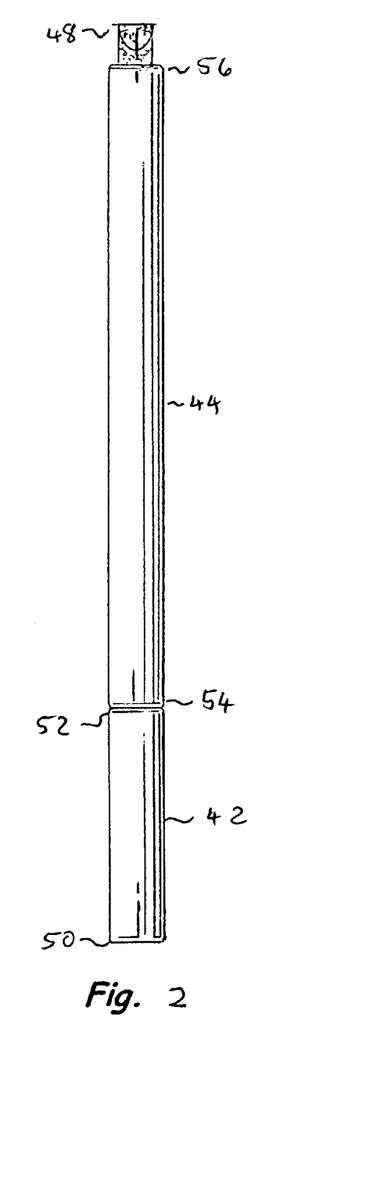
FIG. 2 is a side view thereof.

FIG. 2, an enlarged side view of a preferred embodiment of the dispenser 40, shows the first segment 42 including a closed first segment rear end 50 and a first segment front end 52; the second segment 44 including a second segment rear end 54 and a second segment front end 56, and the applicator 48. The first segment front end 52 is joined to the second segment rear end 54. The applicator 48 projects forward and is disposed proximate the second segment front end 56.

Figure 3:
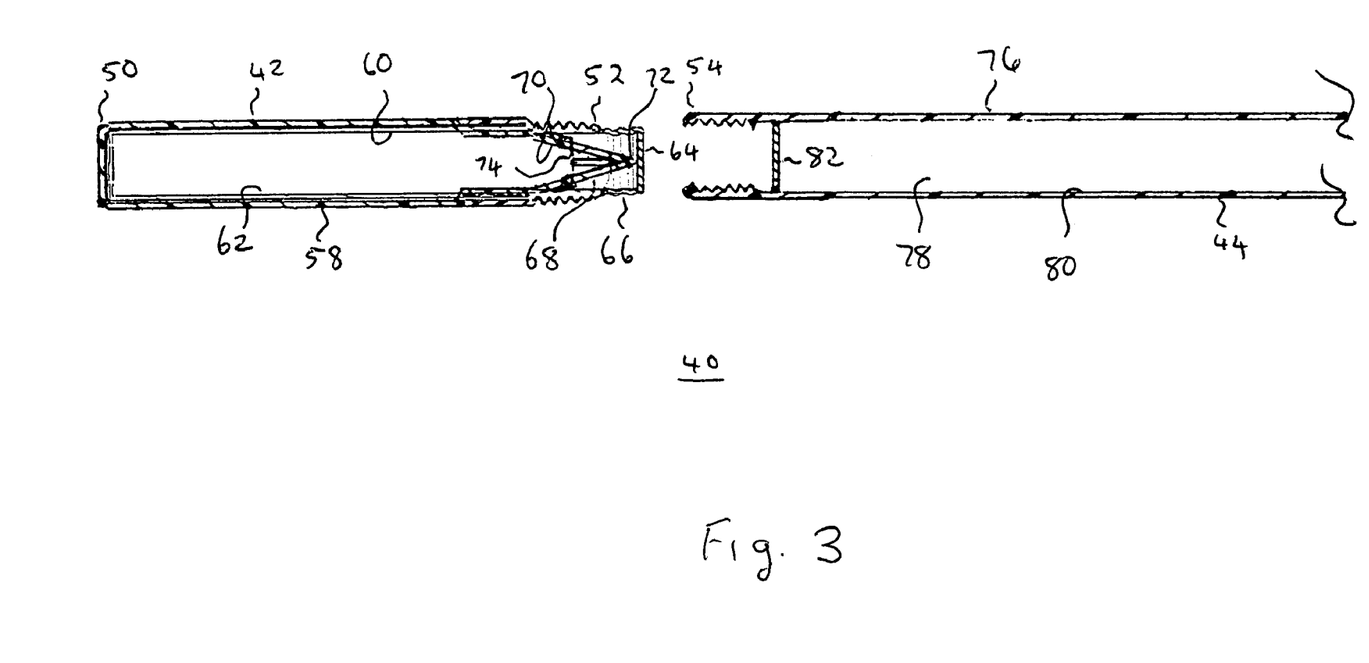
FIG. 3 is a side sectional view thereof.

FIG. 3, a side view of a preferred embodiment of the dispenser 40, shows the first segment 42 and part of the second segment 44 including the second segment rear end 54. The first segment 42 includes a closed first segment rear end 50, a tubular first segment body 58, and an externally threaded open first segment front end 52. A sealed first reservoir 60 is disposed within the first segment body 58 and comprises a tubular first reservoir body 62, a frangible first reservoir front end surface 64 projecting forward of the first segment front end 52, and a longitudinally compressible first reservoir crumple zone 66. A first rupturing member 68 is stabilized within the first reservoir 60 and comprises a bifurcated first thrusting member 70, a first cutting edge 72, and a first spreading member 74 attached thereto and disposed proximate the first reservoir front end surface 64. The first thrusting member 70 may be formed integrally with the first reservoir body 62 or it may be braced within the first reservoir 60, so long as it resists rearward displacement relative to the first segment 42 when the first reservoir body 62 is disposed against the closed first segment rear end 50.

With continued reference to FIG. 3, the second segment 44 comprises a tubular second segment body 76 and an internally threaded open second segment rear end 54. A second reservoir 78 is disposed within the second segment body 76 and comprises a tubular second reservoir body 80 and a frangible second reservoir rear end surface 82. The second reservoir 78 is supported within the second segment 44 so as to resist forward displacement relative to the second segment 44. The second segment rear end 54 and the first segment front end 52 are adapted for mutual threaded engagement.

Figure 4:
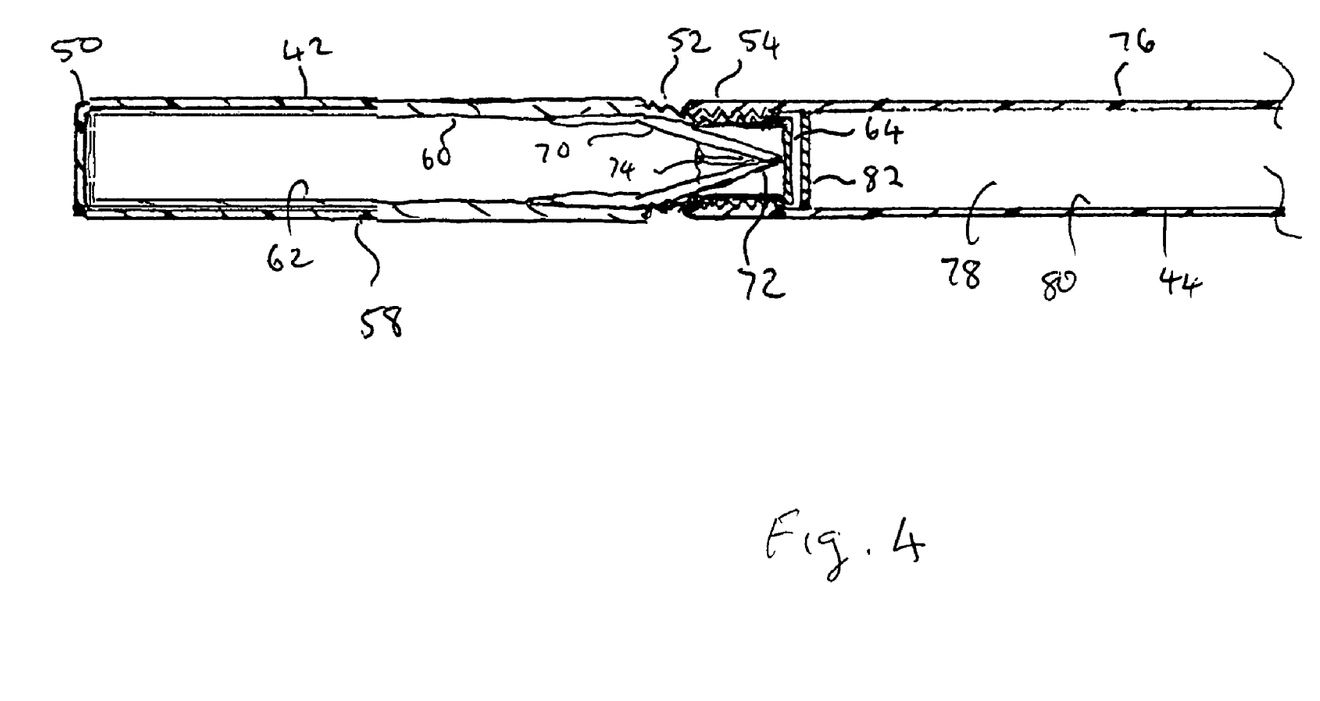
FIG. 4 is a side sectional view thereof.

FIG. 4, a side view of the embodiment of FIG. 3, shows the first segment front end 52 partially screwed into the second segment rear end 54, the first cutting edge 72 and the first reservoir front end surface 64 being proximate the second reservoir rear end surface 82.

Figure 5:
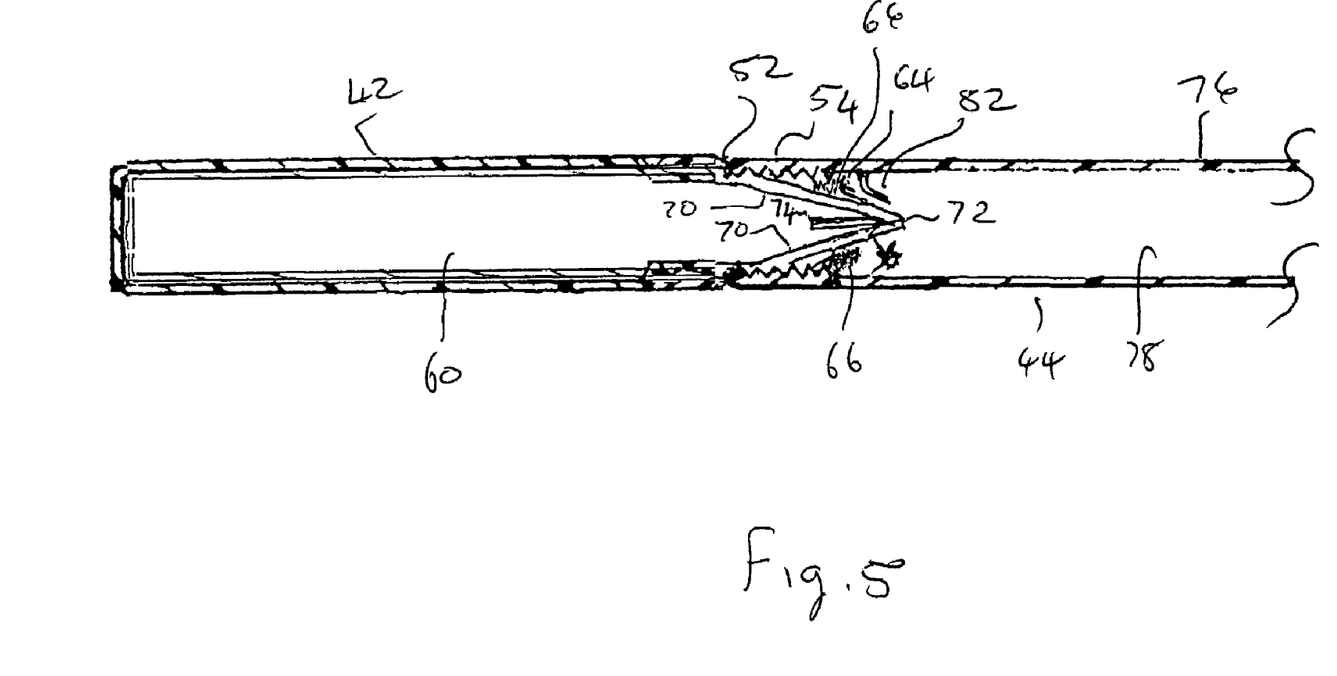
FIG. 5 is a side sectional view thereof.

FIG. 5, a side view of the embodiment of FIG. 3, shows the first segment front end 52 completely screwed into the second segment rear end 54. The first reservoir front end surface 64 has interfered longitudinally with the second reservoir rear end surface 82. The first reservoir crumple zone 66 has been compressed, allowing the first reservoir front end surface 64 to be displaced rearwardly onto the first cutting edge 72. The first cutting edge 72 has pierced the first reservoir front end surface 64 and the second reservoir rear end surface 82, both of which are thereafter held open by cooperation of the first cutting edge 72, the first thrusting member 70, and the first spreading member 74. The held-open first reservoir front end surface 64 and second reservoir rear end surface 82 and the bifurcated first thrusting member 70 establish fluid communication between the first reservoir 60 and the second reservoir 78.

FIG. 6, a side view of the embodiment of FIG. 3, shows the second segment 44 and the third segment 46 and a part of the first segment 42 including the first segment front end 52 screwed into the second segment rear end 54. The second segment 44 comprises an open, internally threaded second segment front end 56. The second reservoir 78 comprises a frangible second reservoir front end surface 84 disposed within the second segment body 76 and proximate the second segment front end 56.

With continued reference to FIG. 6, the third segment 46 comprises an externally threaded tubular third segment body 86 to which are attached a rearward-projecting second rupturing member 88 and a forward-projecting applicator 48. The second rupturing member 88 comprises a rearward-projecting bifurcated second thrusting member 90 affixed to the third segment 46 and a second cutting edge 92 and a second spreading member 94 formed distally thereon. The applicator 48 is formed of a porous, fibrous, or ducted material capable of conducting and dispensing a liquid. The third segment body 86 and the second segment front end 56 are adapted for mutual threaded engagement. It will be appreciated that after the third segment 46 is fully screwed into the second segment front end 56, the second cutting edge 92 has pierced the second reservoir front end surface 84, which is thereafter held open by cooperation of the second cutting edge 92, the second thrusting member 90, and the second spreading member 94. The held-open second reservoir front end surface 84 and the bifurcated second thrusting member 90 establish fluid communication between the second reservoir 78 and the applicator 48.

The first segment 42 and second segment 44 may comprise a polymeric structure stiff enough to be manually grasped and twisted without buckling or cracking; strong enough and hard enough to bear the longitudinal force of propelling a pointed cutting edge through a frangible membrane; and hard enough to generate this force from torque by threaded engagement. Ideally, the first segment front end 52, second segment rear end 54, second segment front end 56, and third segment 46 should be plastic enough and smooth enough to confine liquid contents under light pressure without any need for additional washers or o-rings.

The first reservoir body 62 and the second reservoir body 80 may comprise a polymeric structure stiff enough to resist longitudinal compression except in the first reservoir crumple zone 66. The first reservoir front end surface 64, second reservoir rear end surface 82, and second reservoir front end surface 84 may comprise a polymeric structure frangible enough to be pierced by a pointed cutting edge. Low or medium density polyethylene, polypropylene, and other common container materials are contemplated. A metallic, glass, ceramic, or composite reservoir material may in some cases be preferred for opacity or impermeability.

The first thrusting member 70, first cutting edge 72, and first spreading member 74 may comprise a polymeric structure having sufficient stiffness and hardness to pierce a frangible membrane. High density polyethylene, polycarbonate, polystyrene, and polyvinyl chloride are contemplated, although metal, glass, ceramic, or wood may be preferred.

Figure 7:
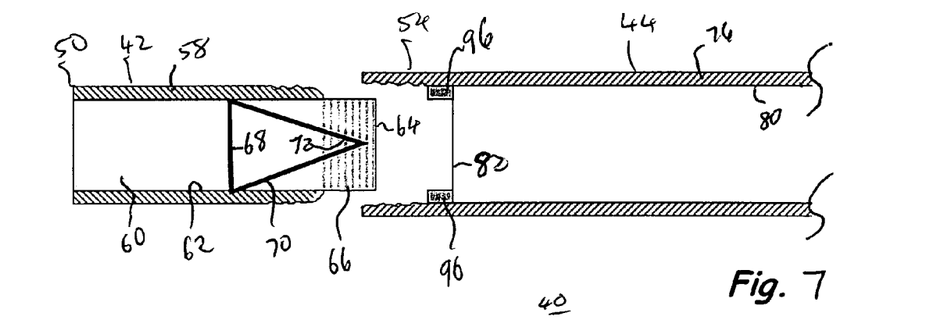
FIG. 7 is a side sectional view of an exemplary embodiment of a hair colorant dispenser in accordance with the present invention.

FIG. 7, a side view of another preferred embodiment of the hair colorant dispenser 40 in accordance with the present invention, shows the first segment 42 and part of the second segment 44 including the second segment rear end 54. Also shown are the first segment 42, a closed first segment rear end 50, a tubular first segment body 58, an externally threaded open first segment front end 52, a sealed first reservoir 60 disposed within the first segment body 58 and comprising a tubular first reservoir body 62, a frangible first reservoir front end surface 64 projecting forward of the first segment front end 52, and a longitudinally compressible first reservoir crumple zone 66; a first rupturing member 68 stabilized within the first reservoir and comprising a bifurcated first thrusting member 70 and a first cutting edge 72 attached thereto and disposed proximate the first reservoir front end surface 64.

With continued reference to FIG. 7, also shown is the second segment 44 comprising a tubular second segment body 76 and an internally threaded open second segment rear end 54; a second reservoir 78 disposed within the second segment body 76 and comprising a tubular second reservoir body 80 and a frangible second reservoir rear end surface 82 and being supported within the second segment 44 so as to resist forward displacement relative to the second segment 44; the second segment rear end 54 and the first segment front end 52 being adapted for mutual threaded engagement. An elastic ring seal 96 is disposed within the second segment body 76 adjacent and to the rear of the second reservoir rear end surface 82. The ring seal 96 may be formed of rubber, silicone, or any suitable washer-forming or gasket-forming material.

Figure 8:
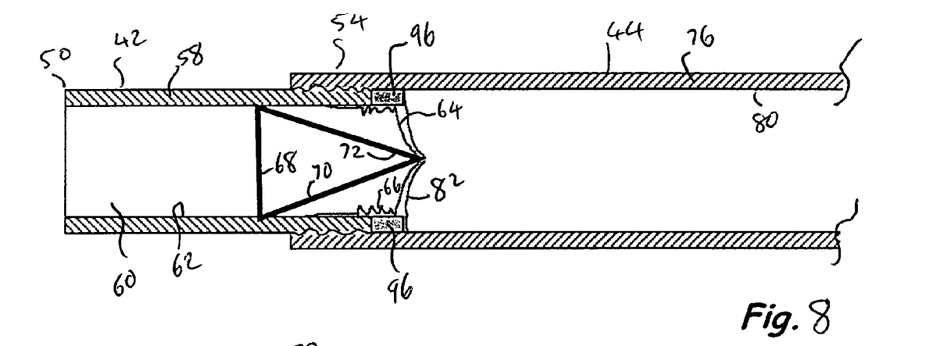
FIG. 8 is a side sectional view thereof.

FIG. 8, a side view of the embodiment of FIG. 7, shows the first segment front end 52, the structures thereof being already identified with reference to FIG. 7, partially screwed into the second segment rear end 54, the first cutting edge 72 being advanced into and displacing the first reservoir front end surface 64 and the second reservoir rear end surface 82, the seal 96 being trapped in a space defined by the first reservoir body 62, the first segment front end 52, the second segment rear end 54, and the second reservoir front end surface 84.

Figure 9:
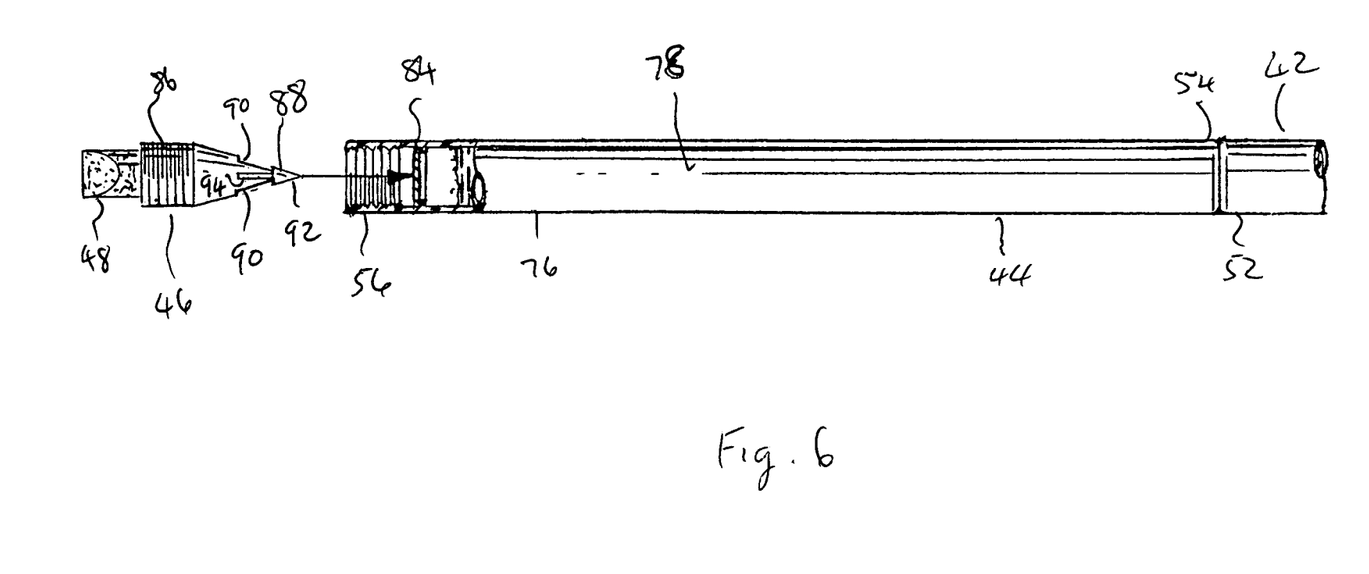
FIG. 9 is a side sectional view thereof.

FIG. 9, a side view of the embodiment of FIG. 7, shows the first segment front end 52 completely screwed into the second segment rear end 54. The first cutting edge 72 has pierced the first reservoir front end surface 64 and the second reservoir rear end surface 82, both of which are held open by cooperation of the first cutting edge 72, the first thrusting member 70, and the first spreading member 74. The held-open first reservoir front end surface 64 and second reservoir rear end surface 82 and the bifurcated first thrusting member 70 establish fluid communication between the first reservoir 60 and the second reservoir 78. The seal 96 helps to prevent leakage of liquid between the first segment front end 52 and second segment rear end 54. The sealing engagement of the third segment 46 to the second segment front end 56 may be enhanced in a similar manner.

This exemplary embodiment transmits longitudinal force to a single cutting edge to reliably rupture the first reservoir front end surface 64 and the second reservoir rear end surface 82, the resistance being supplied by the second reservoir 78 and ultimately the second segment 44.

Figure 10:
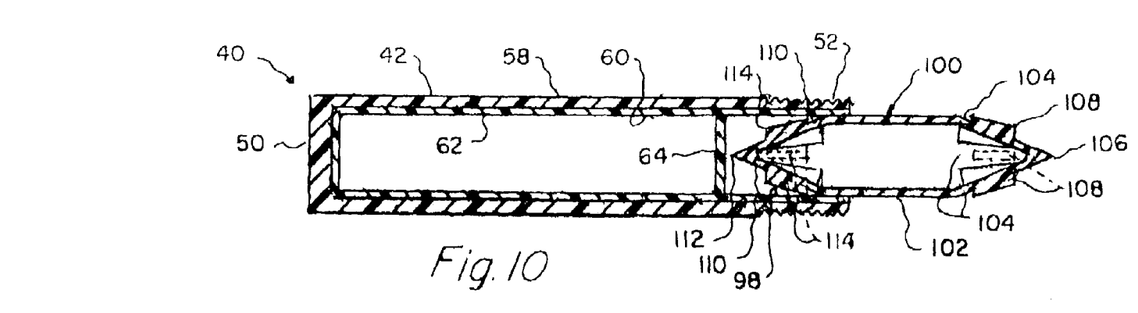
FIGS. 10, 10a, and 10b show a side sectional view, a perspective view, and a cut-away perspective view, respectively, of portions of an exemplary embodiment of a hair colorant dispenser in accordance with the present invention.
Figures 10A, 10B:
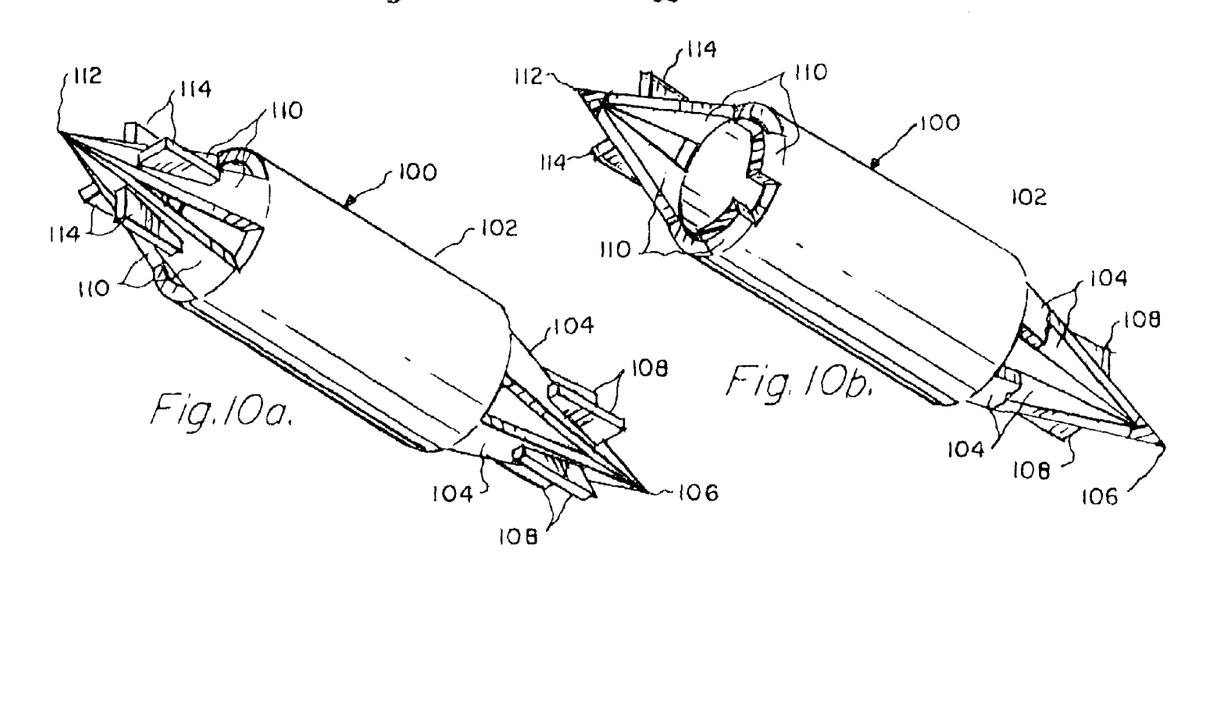

FIG. 10 shows a side sectional view of another exemplary embodiment of the hair colorant dispenser 40 in accordance with the present invention comprising a first segment 42 including a closed first segment rear end 50, a tubular first segment body 58, and an externally threaded open first segment front end 52. A sealed first reservoir 60 is disposed within the first segment body 58 and comprises a tubular first reservoir body 62, a frangible first reservoir front end surface 64, and an open-ended tubular lining 98 projecting forward thereof. A double-ended, coupling rupturing member 100 is stabilized within the lining 98 and projects therefrom to a distance forward of the first segment front end 52. The double-ended, coupling rupturing member 100 comprises a tubular connector 102, a front punch 104 including a cruciform front cutting edge 106 and a cruciform front stop 108, and a rear punch 110 including a cruciform rear cutting edge 112 and a cruciform form rear stop 114. FIGS. 10a and 10b show a perspective view and a cut-away perspective view, respectively, of the rupturing member 100.

Figure 11:
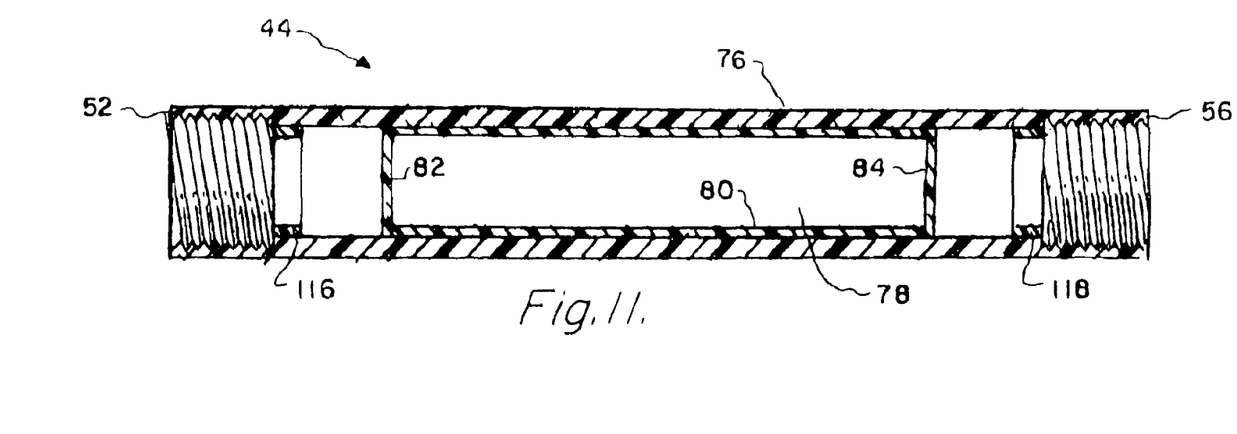
FIG. 11 is a side sectional view thereof.

FIG. 11, a side view of the embodiment of FIG. 10, shows the second segment 44 comprising a tubular second segment body 76, an internally threaded open second segment rear end 54, and an internally threaded open second segment front end 56. A second reservoir 78 is disposed within the second segment body 76 and comprises a tubular second reservoir body 80, a frangible second reservoir rear end surface 82, and a frangible second reservoir front end surface 84. The second reservoir 78 is supported within the second segment 44 so as to resist longitudinal displacement relative to the second segment 44. The second segment rear end 54 and the first segment front end 52 are adapted for mutual threaded engagement. An elastic ring rear seal 116 is disposed within the second segment body 76 adjacent and to the rear of the second reservoir rear end surface 82. An elastic ring front seal 118 is disposed within the second segment body 76 adjacent and to the rear of the second reservoir front end surface 84. Alternatively, the second reservoir 78 may be modified to form both forward-projecting and rearward-projecting linings comparable to the lining 98 formed on the first reservoir 60; the linings may be formed of a moderately plastic material capable of sealing the engagement between the first segment 42 and the second segment 44 or between the second segment 44 and the third segment 46.

Figure 12:
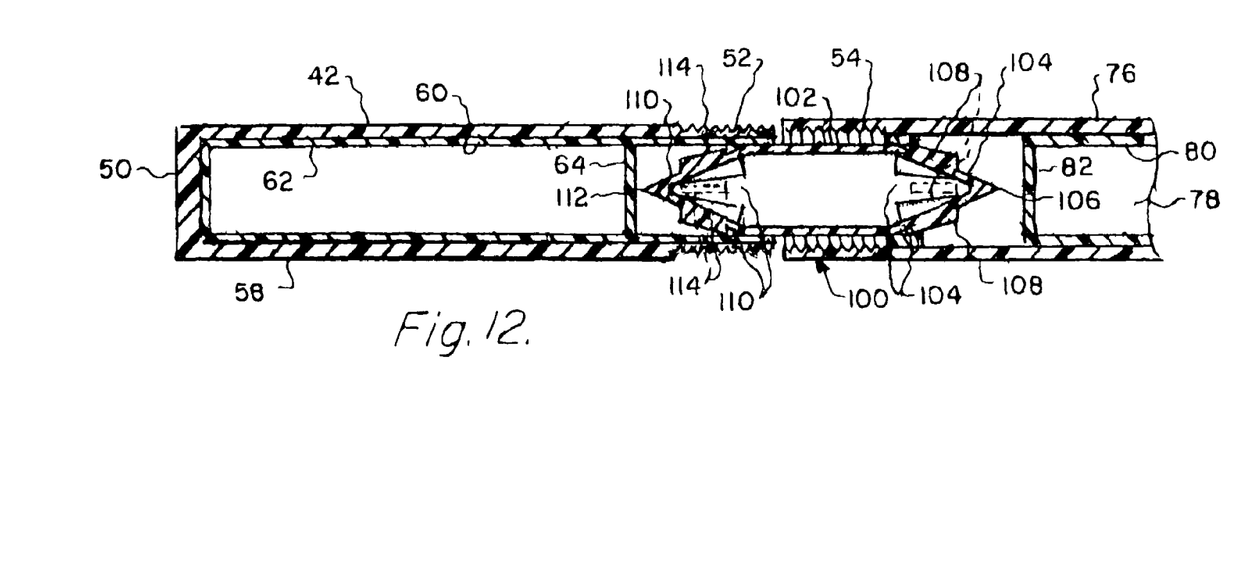
FIG. 12 is a side sectional view thereof.

FIG. 12, a side view of the embodiment of FIG. 10, shows the first segment front end 52 partially approximated to the second segment rear end 54. The connector 102 is shown stabilized within the lining 98 and partly engaged with the rear seal 116. The rear punch 110 is proximate the first reservoir front end surface 64. The front punch 104 is proximate the second reservoir rear end surface 82.

Figure 13:
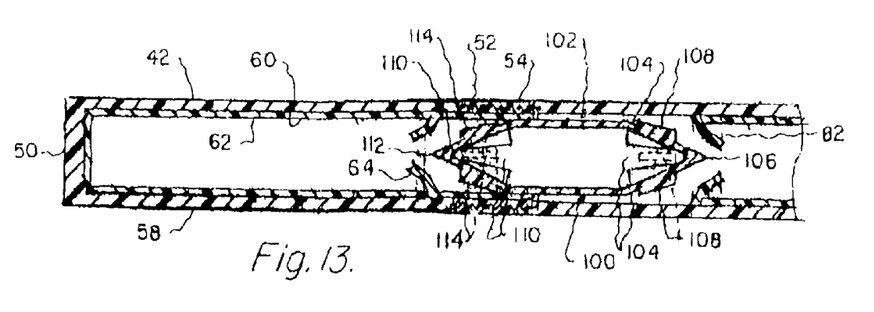
FIG. 13 is a side sectional view thereof.

FIG. 13, a side view of the embodiment of FIG. 10, shows the first segment front end 52 completely screwed into the second segment rear end 54. The cruciform rear punch 110 has pierced the first reservoir front end surface 64. The cruciform rear stop 114 has interfered with the first reservoir front end surface 64 and is thereby urged forward. The cruciform front punch 104 has pierced the second reservoir rear end surface 82. The cruciform front stop 108 has interfered with the second reservoir rear end surface 82 and is thereby urged rearward. The connector 102 assures that the frontward and rearward force are balanced by piercing both the first reservoir front end surface 64 and the second reservoir rear end surface 82, rather than advancing excessively beyond one and piercing the other only partially or not at all. The front punch 104, front stop 108, and rear punch 110, rear stop 114, and connector 102 cooperate to hold open the ruptured first reservoir front end surface 64 and second reservoir rear end surface 82 and to establish fluid communication between the first reservoir 60 and the second reservoir 78.

Figure 14:
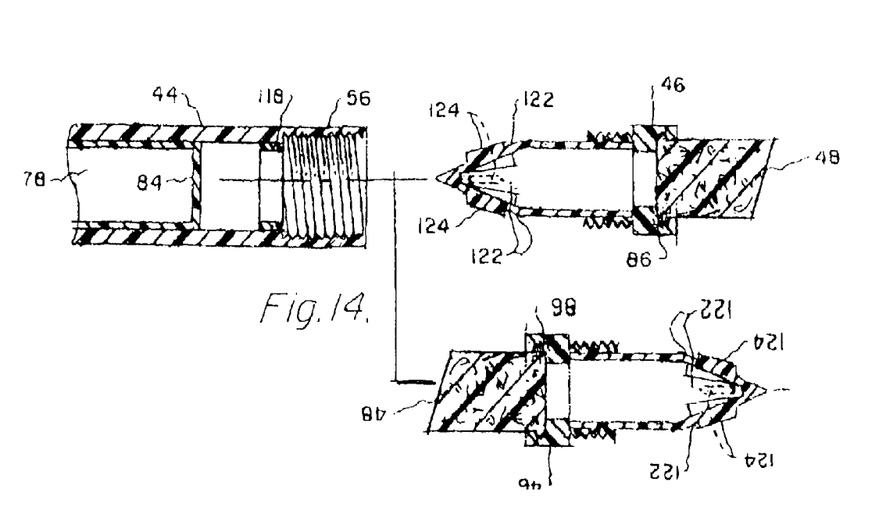
FIG. 14 is a side sectional view thereof.

FIG. 14, a side view of the embodiment of FIG. 10, shows part of the second segment 44 and the entire third segment 46, the third segment 46 comprising an externally threaded tubular third segment body 86 to which are attached a rearward-projecting single-ended rupturing member 120 and a forward-projecting applicator 48. The single-ended rupturing member 120 comprises a rearward-projecting third punch 122 and third stop 124 formed distally thereon. The applicator 48 is formed of a porous, fibrous, or ducted material capable of conducting and dispensing a liquid. The third segment body 86 and the second segment front end 56 are adapted for mutual threaded engagement. It will be appreciated that when the third segment 46 is fully screwed into the second segment front end 56, the single-ended rupturing member 120 will have engaged the front seal 118, the third punch 122 will have pierced the second reservoir front end surface 84, and the third stop 124 will thereafter cooperate with the third punch 122 to hold open the second reservoir front end surface 84, thereby establishing fluid communication between the second reservoir 78 and the applicator 48 as indicated by the arrow in the cut-out view.

FIG. 14 also shows the third segment 46 reversed so as to be insertable in a backward orientation into the second segment front end 56.

This exemplary embodiment balances the forces exerted on the front punch 104 and the rear punch 110 of the double-ended rupturing member, thereby assuring reliable rupture of two reservoir ends surfaces.

With a single twisting operation, all described embodiments of the present invention provide for reliable rupture of all three frangible reservoir end surfaces in order to mix the contents of the first reservoir 60 and the second reservoir 78 and to dispense the mixed contents.

Optionally, the first segment body 58 and the second segment body 76 may be squeezed to facilitate mixing (liquid may be forced back and forth between the first reservoir 60 and the second reservoir 78). Optionally, gravity and a small volume of air or other gas may be used to mix the contents by inverting the dispenser 40 several times. Optionally, the contents may quickly be delivered to the applicator 48 by squeezing one or both of the first segment 42 and the second segment 44.

Optionally, a cap may be provided to protect the applicator 48. Optionally, the applicator 48 may be designed to be substantially shorter than the rupturing member and the third segment 46 may be externally threaded so as to engage the second segment front end 56 with the applicator 48 facing the second segment front end 56. With the second segment 44 and the third segment 46 so joined, the applicator 48 (which may be soft and easily damaged or soiled) may be protected from external impacts and, at the same time, the rupturing member is kept completely away from the second reservoir front end until the time of use. For dispensing contents, the third segment 46 is unscrewed, reversed, and screwed back onto the second segment 44.

Optionally, the first segment rear end 50 may be externally threaded to engage the second segment rear end 54. Thus, the dispenser 40 may be shipped with the first rupturing member 68 (or the front punch 104, as the case may be) positioned safely away from the second reservoir rear end surface 82. If this is done, a cap should be provided to protect the first reservoir front end surface 64 from impacts and to prevent ejection of the first reservoir 60 (or of the double-ended rupturing member, as the case may be).

It is to be understood that internal threading and external threading may be interchanged, that a lining may in some cases be interchanged with a ring seal, and that both the lining and the ring seal can be omitted if the segments can be made to sealingly engage without a lining or seal.

It is to be understood that the double-ended rupturing member could be broken into equal or unequal parts and the parts apportioned between the first segment 42 and the second segment 44.

It is to be understood that the first rupturing member 68 could be transferred from the first reservoir 60 to the second reservoir 78 and inverted.

It is to be understood that the second rupturing member 88 or the third punch 122 (each having been disclosed as projecting rearwardly from the third segment 46) may be omitted if an additional rupturing member were to be so disposed within the second reservoir 78 that the second reservoir front end surface 84 were rupturable upon compression of the second reservoir 78 when the third segment 46 is screwed into the second segment front end 56 surface. The second reservoir 78 could, for example, have a crumple zone such that the second reservoir front end surface 84 and the second reservoir rear end surface 82 are pierced by opposite ends of a single rupturing member disposed within the second reservoir 78. The first reservoir 60 could in such a case be supplied without a crumple zone, so that the first reservoir front end surface 64 is ultimately pierced by the same cutting edge or punch that pierces the second reservoir rear end surface 82. Indeed, a double-ended rupturing member of the type described with reference to FIG. 10 could be provided with an elongated connector 102 and could be disposed within the second reservoir 78 to rupture three end surfaces. In such an arrangement, the second reservoir 78 should have sufficient freedom of longitudinal movement and sufficient longitudinal compressibility to allow for the balancing of forces so that the rupturing member will adequately pierce all three membranes. This arrangement would be advantageous in that there would be no externally projecting cutting edges nor any externally projecting double-ended rupturing member to be dislodged or damaged by mishandling or to inflict injury on persons.

While the foregoing detailed description has described several embodiments of a hair colorant dispenser 40 in accordance with the present invention, it is to be understood that the above description is illustrative only and not limiting of the disclosed invention. Indeed, it will be appreciated that the embodiments discussed above and the virtually infinite embodiments that are not mentioned could easily be within the scope and spirit of the present invention. Thus, the present invention is to be limited only by the claims as set forth below.

What is claimed is:

1. A hair colorant mixing and dispensing apparatus, comprising endwise serially sealingly engageable first, second and third tubular segments, a double-ended rupturing member disposed between said first and second segments, and a single-ended rupturing member disposed between said second and third segments;

said first segment defining an interior including a first reservoir;

said second segment defining an interior including a second reservoir;

said third segment defining an interior including an applicator communicating with said interior;

said double-ended rupturing member including a tubular connector adapted for sliding and stabilizing endwise internal engagement with said first and second segments;

said double-ended rupturing member including front and rear punches, each of said punches including a cutting edge, including a base formed on said rupturing member, a point, and a plurality of perforations between said base and said point, said punches being adapted for rupturing one of said first and second segments, each of said punches including a stop including a plurality of lateral projections located between said base and said point, said lateral projections being adapted for holding open a ruptured one of said first and second segments;

said first and second segments when so engaged defining a range of relative longitudinal displacement including first and second relative positions;

engagement in said first position, said second position, and all intermediate positions forming a seal between proximate ends of said segments to prevent fluid leakage therefrom engagement in said second position resulting in the compression of said double-ended rupturing member between said first and second segments, thereby rupturing proximate ends of said segments and holding said ruptured ends open for facilitating the passage of fluid;

said single-ended rupturing member including a tubular connector adapted for sliding and stabilizing endwise internal engagement with at least one of said second and third segments;

said single-ended rupturing member including a rear punch, said rear punch including a cutting edge, including a base formed on said rupturing member, a point, and a plurality of perforations between said base and said point, said punches being adapted for rupturing said second segment, said rear punch including a stop including a plurality of lateral projections located between said base and said point, said lateral projections being adapted for holding open said ruptured second segment;

said second and third segments when so engaged defining a range of relative longitudinal displacement including first and second relative positions;

engagement in said first position, said second position, and all intermediate positions forming a seal between proximate ends of said segments to prevent fluid leakage therefrom engagement in said second position resulting in the compression of said single-ended rupturing member between said second and third segments, thereby rupturing said second segment proximate said third segment and holding said ruptured second segment open.

2. A hair colorant mixing apparatus as set forth in claim 1, wherein said applicator comprises a porous wick.

3. A hair colorant mixing and dispensing apparatus as set forth in claim 1, wherein each of said punches comprises a plurality of base members joined distally to form a common cutting edge and to define at least two fluid passages around said plurality of base members.

4. A hair colorant mixing and dispensing apparatus as set forth in claim 1, wherein said third segment has a front end surface in which said applicator is mounted and said second segment has a front end surface adapted to engage said front end surface of said third segment, and aid third segment is mountable on said front end of said second segment in a backwards orientation such that said applicator is disposed adjacent said front end surface of said second segment.

5. A hair colorant mixing and dispensing apparatus as set forth in claim 4, wherein:

said rear end surface of said third segment is engageable with said front end surface of said second segment in a fluidly sealed and secured configuration wherein said second rupturing means ruptures said front end surface of said second segment; and said front end surface of said third segment is engageable with said front end surface of said second segment in a secured configuration wherein sufficient clearance exists for said applicator to be disposed forward of said front end surface of said second segment.

* * * * *